US00PP08141P

United States Patent [19]

Austin

[11] Patent Number: Plant 8,141

[45] Date of Patent: Feb. 16, 1993

[54] ROSE PLANT—'AUSCAT'

[75] Inventor: David C. H. Austin, Albrighton, England

[73] Assignee: David Austin Roses, Albrighton, England

[21] Appl. No.: 623,289

[22] Filed: Dec. 6, 1990

[51] Int. Cl.[5] ..... A01H 5/00

[52] U.S. Cl. ..... Plt./1

[58] Field of Search ..... Plt. 1

*Primary Examiner*—Howard J. Locker

*Attorney, Agent, or Firm*—Ladas & Parry

[57] ABSTRACT

A new variety of rose plant of the shrub class distinctive in its character by its fully double, soft white flowers with abundant continual blooming.

1 Drawing Sheet

BACKGROUND OF THE INVENTION

The present invention relates to a new and distinct variety of shrub roses, said new variety originating as a single seedling resulting from a definite effort to produce an improvement in this class of rose.

BRIEF SUMMARY OF THE INVENTION

Primary features of this new variety which connote a distinctive advance over existing types are the vigorous, abundant and continual blooming that occurs for 5 months taken with the perfection of the fully double flowers of an old-fashioned shape, more particularly apparent in the accompanying illustration of a specimen thereof.

BRIEF DESCRIPTION OF THE DRAWING

The accompanying illustration shows typical cultivar flowers of this new cultivar in various stages of development, depicted in color as nearly true as is possible to make the same in color illustrations of this character.

DETAILED BOTANICAL DESCRIPTION

The following is a detailed description of the new variety, color terminology being in accordance with the "Methuen Handbook of Color" published by Eyre Methuen Ltd (1963).

Variety denomination (in accordance with the UPOV Convention):Auscat

*Cultivar* trade name: Winchester Cathedral.

Type: Hardy, bush, outdoor, garden decoration, cut flowers.

Class: Shrub.

Propagation: The variety holds its distinguishing characteristics through succeeding propagations by budding.

Asexual reproduction of the new cultivar by budding has taken place at a nursery in Albrighton, Nr. Wolverhampton, England and was derived as follows:

Female parent (seed parent): Wife of Bath × Un-named seedling (both non-patented).

Male parent (pollen parent): Mme Caroline Testout × The Friar (both non-patented).

The operation of the artificial pollination is therefore expressed by the following (Wife of Bath × Mme Caroline Testout) × The Friar.

The following observations are made of specimens grown outdoors in England.

PLANT DESCRIPTION.

Plant:

*Height.*—120 cm.

*Habit.*—Tall, upright and bushy.

Branches:

*Young stems.*—Color: 29D7 greyish green. Texture: Red glandular hairs. Thorns: 5–12 per internode. Basal width: 1–3 mm. Height: 1–3 mm. Color: brownish red 8E7.

*Old stems.*—Color: 29E8 Dark green. Texture: Red Glandular hairs and/or thorns. Thorns: Many, 10–20 per internode. Basal width: 1–6 mm. Height: 1–5 mm. Color: reddish brown 8E7.

LEAVES

Stipules:

*Length.*—1.8–2.2 mm.

*Width.*—5–8 mm.

*Angle of wingtips to petiole.*—Variable, but most often less than 45°.

*Color.*—Mid green.

*Margins.*—Edged with red glandular hairs along central line (petiole) with distinct 11E6 violet brown blush.

*Shape.*—Wings convex, clasping at base.

Petiole:

*General description.*—Length: 8–11 cm. Upperside color: 29F7 Dark green with violet brown 11E6 blush. Groove/hairs/thorns: Red glandular hairs, no thorns. Underside: Color: 29D7 Greyish green. Hair/thorns: Sparse red glandular hairs. Leaflets: Number: 3 to 7 (mainly 5). Shape: Ovoid with cuspidate tip. Serration: Dentate. Texture: Tough and leathery.

*General effect of foliage.*—Medium dense. Color: Young foliage. Upperside: 29E8 Deep green. Underside: 29D6 Greyish green with 11F7 violet brown blush. Margins: 11F7 Violet brown. Adult foliage: Upperside: Dark green 27F7. Underside: Spinach green 29E6.

INFLORESCENCE

Number of flowers per stem: Very variable 1–15.

Peduncle:

*Length.*—3.0–4.5 cm.

*Color.*—Medium green.

*Thorns/hairs.*—Medium dense red glandular hairs.

Sepals:

*Upperside color.*—29D7 greyish green, brownish red blush 10C6 occasional ensiform appendages.

*Outer margins.*—Sparse red glandular hairs.

*Inner margins.*—Entire, edged with fine white downy hairs.

*Underside color.*—30C7 Spring green.

*Texture.*—Smooth.

*Sepal length.*—1.7–2.5 cm.

*Bud shape.*—Round, with cuspidate tip before bud break.

*Length.*—2.5–3.0 cm before bud break.

*Max. width.*—1.0–1.2 cm before bud break.

*Color when opening.*—5A3/4 pale/light orange with geranium 11B7 blush.

*Flower shape.*—As a flattened cup. Outer petals recurved towards stem on the blooms as they age.

*Diameter.*—5.0–6.5 cm.

Flower color when opening.—Upperside: 3A3 pale yellow. Underside: 4A3 cream.

*Flower color when blooming.*—Upperside: 4A2 Yellow white, but lighter. Underside: 4A2 as above, but slightly deeper.

*Flower coloring when finished blooming.*—Upperside: 4A1 white, basal tip yellow 3A3/4. Underside: 4A1 white, basal tip yellow 3A3/4.

Length of blooming season at production location: From June to October.

Fragrance: Sweet.

Lasting quality: Good. Range in number of days on plant is 10–12 days. Range in number of days as cut flowers is 6–9 days.

Petals.

*Shape.*—Outside: Width 2.5–4.0 cm/length 3.0–3.5 cm. Heart shaped, apex and bilobed, margin slightly irregular, narrowing to truncate base. Middle: Width 2.5–4.0 cm/length 3.0–3.5 cm. Roughly ovoid, apex wide and flattish irregular or bilobed, narrowing to v-shaped or truncate base. Inside: Fairly irregular. Round ovoid, apex rounded or irregularly lobed with some narrowing to a v-shaped true petal shape and others growing from the filaments and are not true petal shape, that is, staminate. Width 1.0–1.5 cm. Length 1.5–2.0 cm.

*Texture.*—Fairly solid.

*Number.*—80–85.

*Cleaning.*—Average good petals fall reasonably easily to leave a tidy looking rose but not quite as quickly as desired.

Stamens:

*Number.*—52–60 but on average 55.

*Anthers.*—4A7 Reddish yellow.

*Filaments.*—2A4 pastel yellow 4.5 mm.

Pistils:

*Number.*—46–53 but on average 50.

*Stigmas.*—30A2 greenish white/1A2 yellowish/-white.

*Styles.*—30B7 yellowish green 5.9 mm.

Receptacle:

*Color.*—30D8 deep green with greyish.

*Texture.*—Smooth.

*Size.*—Length 1.0–1.2 cm. Width 0.8–0.9 cm.

THE DEVELOPMENT

Vegetation: Vigorous.

Blooming: Abundant and continual.

Aptitude to bearing fruits: None.

Resistance to frost: Good.

Resistance to disease: Very good.

I claim:

1. A new and distinct variety of rose plant of the shrub class, characterized as to novelty by its fully double flowers of white, with abundant and continual blooming and the coloring and shaping of the flower being substantially as shown and described.

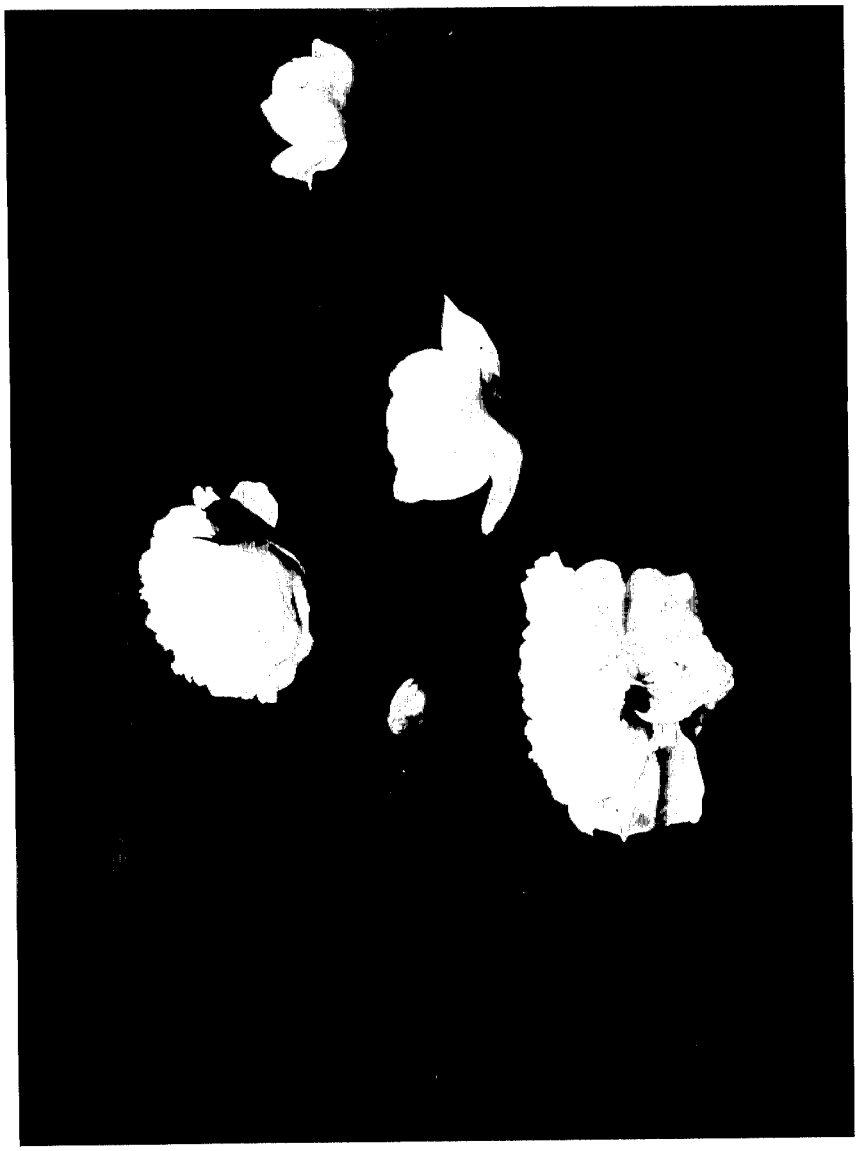

* * * * *